(12) United States Patent
Kunath-Fandrei et al.

(10) Patent No.: US 8,986,289 B2
(45) Date of Patent: Mar. 24, 2015

(54) METHOD FOR MARKING COAGULATION SITES OF A RETINA AND SYSTEM FOR COAGULATING THE RETINA

(75) Inventors: Gerald Kunath-Fandrei, Jena (DE); Jenny Dünger, Jena (DE); Rico Fuchs, Jena (DE); Manfred Dick, Gefell (DE)

(73) Assignee: Carl Zeiss Meditec AG, Jena (DE)

( * ) Notice: Subject to any disclaimer, the term of this patent is extended or adjusted under 35 U.S.C. 154(b) by 494 days.

(21) Appl. No.: 13/320,727

(22) PCT Filed: May 14, 2010

(86) PCT No.: PCT/EP2010/002968
§ 371 (c)(1),
(2), (4) Date: Feb. 29, 2012

(87) PCT Pub. No.: WO2010/130456
PCT Pub. Date: Nov. 18, 2010

(65) Prior Publication Data
US 2012/0150159 A1    Jun. 14, 2012

(30) Foreign Application Priority Data

May 15, 2009  (DE) .......................... 10 2009 021 604

(51) Int. Cl.
*A61F 9/007*  (2006.01)
*A61F 9/008*  (2006.01)
(Continued)

(52) U.S. Cl.
CPC .............. *A61F 9/008* (2013.01); *A61F 9/00821* (2013.01); *A61B 18/20* (2013.01); *A61B 2018/00636* (2013.01);
(Continued)

(58) Field of Classification Search
CPC ............ A61F 2009/00897; A61F 2009/00863; A61F 9/008; A61F 9/00821; A61B 2018/2085; A61B 2018/2025; A61B 2019/202; A61B 18/20; A61B 2018/00636
See application file for complete search history.

(56) References Cited

U.S. PATENT DOCUMENTS 6,830,567 B2 * 12/2004 Schuele et al. .................... 606/4
2006/0100677 A1 * 5/2006 Blumenkranz et al. ......... 607/89
(Continued)

FOREIGN PATENT DOCUMENTS

DE          101 35 944 A1      2/2003
DE     10 2005 055 885 A1      5/2007
(Continued)

*Primary Examiner* — Gary Jackson
*Assistant Examiner* — Scott T. Luan
(74) *Attorney, Agent, or Firm* — Patterson Thuente Pedersen, P.A.

(57) ABSTRACT

A method for marking coagulation sites on a retina by application of a light source including: projecting a serial spot sequence from a sequential, one-dimensional series of spots on the retina, wherein the individual spots indicate the coagulation sites; waiting for confirmation of the sequence of individual spots; after confirming, recalculating an automated sequence of steps having a further serial spot sequence and projecting them on the retina according to the first step; and subsequent repeating of the second and third steps. Also, a system for coagulating the retina, having an imaging diagnostic unit, a therapy beam for coagulating coagulation sites, a pilot beam for marking the coagulation sites by a spot sequence, a beam deflecting unit for generating the spot sequence and for positioning the therapy beam, an electronic control unit for controlling the above devices, a software interface, and an interactive interface.

19 Claims, 4 Drawing Sheets (51) Int. Cl.
*A61B 18/20* (2006.01)
*A61B 18/00* (2006.01)
*A61B 19/00* (2006.01)

(52) U.S. Cl.
CPC .. *A61B 2018/2025* (2013.01); *A61B 2019/202* (2013.01); *A61F 2009/00863* (2013.01)
USPC .......................................................... 606/4

(56) References Cited

U.S. PATENT DOCUMENTS

| | | |
|---|---|---|
| 2006/0161145 A1 | 7/2006 | Lin et al. |
| 2008/0015553 A1 | 1/2008 | Zacharias |
| 2008/0033406 A1 | 2/2008 | Andersen et al. |
| 2008/0167642 A1 | 7/2008 | Palanker et al. |
| 2008/0300581 A1 | 12/2008 | Wiechmann et al. |
| 2009/0207874 A1 | 8/2009 | Zimare et al. |
| 2011/0116040 A1 | 5/2011 | Biernat et al. |

FOREIGN PATENT DOCUMENTS

| | | |
|---|---|---|
| DE | 10 2006 019 127 A1 | 10/2007 |
| DE | 10 2008 011 836 A1 | 9/2009 |
| WO | WO 2005/065116 A2 | 7/2005 |
| WO | WO 2007/035855 A2 | 3/2007 |
| WO | WO 2007/051061 A2 | 5/2007 |
| WO | WO 2008/112236 A1 | 9/2008 |
| WO | WO 2009/045286 A1 | 4/2009 |

* cited by examiner

METHOD FOR MARKING COAGULATION SITES OF A RETINA AND SYSTEM FOR COAGULATING THE RETINA

PRIORITY CLAIM

The present application is a National Phase entry of PCT Application No. PCT/EP2010/002968, filed May 14, 2010, which claims priority from German Application No 102009021604.9, filed May 15, 2009, the disclosures of which are hereby incorporated by reference herein in their entirety.

FIELD OF THE INVENTION

The invention relates to a method for marking of coagulation sites on a retina by means of a light source as well as a system for coagulating the retina for executing such a method.

BACKGROUND

The use of focused light from an axial high-pressure lamp for the treatment of various diseases of the retina, e.g., diabetic retinopathy, by means of the light coagulation has been known for decades. Nowadays, the retina is warmed up or coagulated during light coagulation by means of a laser beam, wherein the energy of the laser beam is absorbed by the dark coloring of the pigment epithelium within the retina. As a result, the metabolism is focused on the as yet healthy areas of the retina. In addition, biochemical cofactors are stimulated. This way, the progress of the disease is considerably slowed or stopped.

However, it is hereby disadvantageous that tissue worthy of preservation, particularly the photoreceptor layer located in beam direction in front of the retinal pigment epithelium, is also destroyed. Therefore, solutions have been provided which minimize the destruction of tissue worthy of preservation, wherein the local treatment is terminated once a defined temperature is reached at the coagulation point. Hereby, a temperature-controlled coagulation system with a continuous coagulation laser and a pulsed measuring laser as well as a detector, a control device, and an interrupter is used. Thereby, the coagulation laser is designed in such a way that a coagulation beam is emitted and that the measuring laser generates a temperature-dependent measurement signal for the detector in the target area of the coagulation laser. Thereby, the detector exhibits a temperature sensor that detects a signal which allows for conclusions regarding the temperature at the coagulation point. The signal detected by the detector is transmitted to the control device which activates the interrupter once a predetermined temperature is reached, thereby interrupting the beam of the coagulation laser.

The coagulation points are periodically adjusted manually by the operator who individually triggers the coagulation beam. This is very time-consuming and the success of the treatment greatly depends on the abilities of the operator; therefore, it was suggested in WO 2007/035855 A2, e.g., to provide a system and a method, wherein a pattern of coagulation points is provided from which the operator can choose beforehand and/or combine the various patterns with one another. Thereby, two-dimensional arrangements of coagulation points are considered patterns which, for example, exhibit a matrix of 2×2, 3×3, 4×4, 5×5, etc., wherein the distances of adjacent coagulation points remain constant. This prior art also provides other two-dimensional patterns, e.g., arrangements on a circle and/or on concentric circles, elliptical and sector-shaped arrangements.

However, such fixed patterns of regular geometry are disadvantageous because very often they do not correspond to the morphological conditions of the physiological anomalies. Therefore, recoagulation with a second or third coagulation pattern up to a single-burst coagulation, which was to be overcome with said method, is frequently required for efficiently executing a completely effective panretinal photocoagulation. Even though it is possible with the above-mentioned prior art to achieve a large pattern which leads to an increase in the speed of the treatment, the risk of overcoagulation and/or undercoagulation through the changeable focus remains due to the retinal curvature and/or varying absorption behavior of the present ocular media.

SUMMARY OF THE INVENTION

Therefore, the problem addressed by the invention is that of allowing for a laser treatment, for example retina coagulation, laser trabeculoplasty, or an optimized panretinal photocoagulation, at very high treatment speed, wherein only pathological areas but no healthy areas are coagulated. Thereto, the marking of coagulation sites, visible to the operator before the treatment, by means of a method shall be ensured, and a system for coagulation shall be provided which allows for the execution of such marking.

This problem is solved through a method for marking of coagulations sites on a retina by means of a light source with the features discussed herein. Projecting a serial spot sequence of the light source from a sequential, one-dimensional series of individual spots on the retina by means of a beam deflection unit, wherein the individual spots indicate the coagulation sites. This indicates to the operator beforehand, i.e., before the actual coagulation takes place, on which sites the coagulation is to occur. Waiting for confirmation of the sequence of individual spots by means of entry of a confirmation signal ensures that no coagulation sites are treated which are to be spared, e.g., because they contain healthy tissue. After confirming the sequence of the individual spots, according to the invention, an automated sequence of steps having a further serial spot sequence and projection of the same on the retina is recalculated. The use of a sequential, one-dimensional series of individual spots, which are created automatically, leads, when compared to a manual determination of said individual spots, to a significant increase in speed. Contrary to the provision of very complex two-dimensional and large patterns, the method, according to the invention, is advantageous because a confirmation must be entered by the operator for every individual sequential, one-dimensional series in order to subsequently—this not being subject matter of the method according to the invention—execute the coagulation on said sites. As a result, coagulation of healthy tissue is avoided and only those coagulation sites are accepted which are actually necessary for the healing process. Through the repetition of the above-mentioned steps according to the invention, it is possible to mark a large area of the retina with coagulation points in a short period of time.

In an advantageous development of the invention, the sequential, one-dimensional series of individual spots exhibits equidistant distances and the progression of which is straight or curved as well as continuous or non-continuous. Due to the different indicated possibilities of placing the individual spots, the conditions in respect of the pathological areas of the retina as well as the present ocular media, such as astigmatism or other types of defective vision of the eye to be treated can be taken into account.

A further advantageous development of the invention provides for the temporal series of the spot sequence to have an interval between spots according to one example 1 ns and 5 s, preferably between 1 µs and 1 s, particularly preferred between 40 ms and 0.5 s. The above-mentioned temporal upper and lower limits are advantageous for an expeditious execution of the method while simultaneously ensuring good monitoring by the operator.

In a further advantageous development of the invention, an automated sequence of steps provides for an equidistant translation and/or rotation. As a result, multiple patterns can be produced which can be derived from a very simply arranged basic pattern, i.e., the sequential, one-dimensional series. Once again, it is possible to take into account the individual conditions of the retina to be treated.

Thereby, the sequential, one-dimensional basic pattern can be applied at any random site and completed through translation and/or rotation in random directions.

Hereby, the term "pattern" is used synonymously with the terms "sequence," or "series." The consecutively produced, manipulable individual spots form a first basic sequence, from which an overall pattern is produced through translation and/or rotation.

A further advantageous development of the invention provides for the light source to radiate laser light, particularly in the red range. The use of laser light in the red range has the advantage of producing individual spots which are easily recognizable on the retina by the operator.

A further advantageous development of the invention provides for an active influence by the operator through variation of one or several laser parameters prior to the confirmation of the next spot sequence. This results in an optimal adjustment of the required parameters in a very short period of time, wherein the operator does not have to wait for the system to display the spot sequence required at this moment.

A further advantageous development of the invention provides for the confirmation by means of a joystick, voice recognition, or a foot switch, particularly a multimodal foot switch. By means of the above-mentioned device, a simple and precise input for confirming the series of individual spots suggested by the system can be made by the operator.

A further advantageous development of the invention provides for the confirmation to take place only after the change of positions of the recalculated spot sequence. As a result, the individual conditions of the retina to be treated can be taken into account particularly well because individual series of individual spots suggested by the system can be rejected, and therefore coagulation takes place only at recalculated individual spots which meet the requirements for an intended coagulation but not at unintended sites.

A further advantageous development of the invention provides for the distance between a next spot sequence and a previous spot sequence to be between zero and ten times that of the spot diameter, particularly preferable between 0.8 and 1.5 times the spot diameter. This allows for a variation which extends from a superimposition of the spots, i.e., an enlargement of the spot surface, to a distance with sufficient space between the individual spots. Therefore, a good individual treatment of the retina is possible.

A further advantageous development of the invention provides for a change of the distance of the starting position, orientation, length, inner-sequence distance, type of spot sequence, rotation, translation and/or step length of the spot sequence with reference to the previous spot sequence to be initiated by the operator and/or based on previously determined examination data of the retina. Said very comprehensive option of changing the individual spots—their individual configuration as well as their spatial arrangement to one another—allows in turn for the best possible treatment solely on the intended sites. Since the concrete definition and determination of the above-mentioned characteristics of the spot sequence is possible due to the previously acquired examination data of the retina, a completely automated coagulation, adjusted to the retina treated moments ago, can be automatically executed exclusively on the actual intended sites. The term inner-sequence distance indicates the distance between two adjacent individual spots within the sequence. The inner-sequence distance is not kept constant but changes from one individual spot to the next.

A further advantageous development of the invention provides for a temperature determination of the individual spot during the use of a therapy beam. As a result, only a brief coagulation of the retinal pigment epithelium is realized without damaging the overlying photoreceptor layer. Thereby, the therapy beam is preferably deactivated when a predetermined temperature is reached which is particularly identical for all individual spots.

A further advantageous development of the invention provides for the individual spots to encircle the coagulation sites. This allows for the operator to precisely determine what the treatment area, which is to undergo coagulation through the therapy beam, looks like and whether a coagulation is indeed to be executed over the entire area.

However, the herein described method for marking defined sites on a retina is not only applicable to a subsequent coagulation of the retina but, for example, also for an iridectomy or iridotomy of the iris.

The problem is also solved through a system for coagulating the retina with the features as disclosed herein.

In an example application, the system for coagulating the retina, having an imaging diagnostic unit, a therapy beam for coagulating coagulation sites, a pilot beam for marking the coagulation sites by means of a spot sequence, a beam deflecting unit for generating the spot sequence and for positioning the therapy beam, an electronic control unit for controlling the above devices, a software interface, and an interactive interface, is used for executing the method described above.

By means of the imaging diagnostic unit, the operator can determine prior to executing the coagulation, at which concrete site of the retina said coagulation should be performed since the spot sequences marked by the pilot beam can now be observed. The therapy beam is used for coagulating the coagulation sites which were marked with the pilot beam beforehand. Therapy beam and pilot beam are controlled by a beam deflecting unit in such a way that the spot sequences of the pilot beam are projected onto the retina and that the therapy beam performs the coagulation on the marked individual spots after clearance through the confirmation by means of the confirmation signal. The entire process is controlled by the control unit which particularly controls the activation of the therapy beam as well as the beam deflection within the beam deflecting unit. The entire process is executed via a software interface. By means of the interactive interface, the confirmation by means of the confirmation signal is effected which is necessary for activating the therapy beam once the marking of the individual spots of the coagulation sites were indicated to the operator by means of the pilot beam.

In an example embodiment, the imaging diagnostic unit is a laser slit lamp, a fundus camera, or a scanning laser ophthalmoscope.

A number of light sources, such as LEDs, superluminescent diodes, gas discharge lamps, and particularly lasers are suited as therapy beam. Thereby, a multiwavelength laser, which can emit different colors in the visible range, is preferably used. Particularly preferable are the colors green, yellow, and red. Furthermore, it is also preferable for the multiwavelength laser to emit light in the near infrared range. The different indicated wavelengths make it possible to reach different coagulation depths. Due to the photopigment melanin, the highest absorption takes place in the green wavelength range (from 514-550 nm); the highest absorption of the blood pigment hemoglobin is achieved in the yellow spectral range (550-580 nm); however, coagulation at a high tissue penetration takes place because of the red wavelengths (630-690 nm) or by application wavelength in the near infrared range (e.g., at 810 nm).

For coagulating the retina, pulse durations between 10 ms and 100 ms, particularly between 20 ms and 50 ms, have proven successful for the therapy beam.

Even though pulse durations below 20 ms ensure an almost painless treatment, the effect of the treatment must be expected to be inferior. By contrast, a superior treatment effect must be expected with pulse durations above 50 ms but which can lead to scarring of the treated sites.

A high coagulation effect, wherein resulting scarring diminishes over time, is achieved with pulse durations between 20 ms and 50 ms. Therefore, pulse durations between 20 ms and 50 ms are recommended for the solution for coagulating the retina as described herein.

A further advantageous development of the invention provides for the pilot beam to be a laser diode which preferably radiates in the red range. The resulting markings on the retina—as already described above—are easily identifiable by the operator.

A further advantageous development of the invention provides for the beam deflecting unit to coaxially project the pilot beam and the therapy beam onto the retina. This ensures that the coagulation by application of the therapy beam takes place exactly at the position indicated beforehand by the pilot beam to the operator who cleared said position by means of a confirmation signal. This ensures that the retina is not coagulated in sites which should not be coagulated, for example, because they still contain unimpaired tissue.

A further advantageous development of the invention provides for the beam deflecting unit to exhibit movable lenses, mirrors, or diffractive beam splitters in the beam path. In prior art, these are well-known, reliable devices for beam deflection. Said lenses or mirrors are preferably controlled via motors; this particularly refers to galvanometrically controlled mirrors, piezo scanners, or micromirror arrays.

A further advantageous development of the invention provides for the control unit to be a microcontroller which exhibits at least one input interface and one output interface and which is programmable. This allows for previously determined values about the retina to be treated as well as the present ocular media to be entered into the control unit, which therefore knows the individually required data for the pending treatment and can adjust the respective series of individual spots to the present concrete conditions. As a result, it will periodically not be necessary for the operator to refuse clearance of the displayed series of individual spots and for the system to calculate and display to the operator an alternative series. Instead, every one of the displayed series can be cleared by the operator, leading to an accelerated treatment as well as increased reliability of the treatment.

A further advantageous development of the invention provides also for an interrupter which prevents at least one specific wavelength range of the therapy beam from impinging on the coagulation site. As already described above, the penetration of the radiation of the therapy beam, and therefore the coagulation, can be controlled through the use of different wavelengths. Therefore, the interrupter specifies different penetration depths of the therapy beam at a predetermined individual spot or for an entire series of individual spots. Preferably, said interrupter is a filter which can be introduced into the therapy beam.

A further advantageous development of the invention provides for the interrupter to be a device which deactivates the therapy beam, particularly in the form of an aperture in the area through which the therapy beam passes. As a result, the coagulation can be altogether completed and not only selectively in one or different depths as is the case with the previously described filter.

A further advantageous development of the invention additionally provides for a device for temperature determination for determining the temperature at the coagulation site while the therapy beam is directed at said site. As already described above, the photoreceptor layer above the pigment epithelium to be treated can thereby be excluded from damage. Temperature determination is preferably effected by means of a detector within the device for temperature determination, which records pressure waves from the coagulation site. Since the device for temperature determination is connected to the interrupter, the therapy beam can immediately be deactivated once the predetermined temperature is reached, resulting in the above-mentioned effect, i.e., the photoreceptor layer will not be damaged. Hereby, an indirect connection of the device for temperature determination via the control unit can be provided in addition to the direct connection to the interrupter.

A further advantageous development of the invention provides for the system to be prepared for irradiating every individual spot of the serial spot sequence through the therapy beam with an individual size, form, wavelength, and duration. This also serves the individual treatment of every site of the retina. By adjustment of the parameters of size and form, the treatment area at the respective coagulation site can be precisely adjusted to desired size and form. By wavelength adjustment, a specific depth of coagulation can be achieved within the retina, as already described above. As a result, a depth-modulated laser coagulation is possible for all coagulation sites. Through adjusting the duration, the temperature of the individual coagulation sites can be varied, resulting in the degree of coagulation of the retina. Therefore, a coagulation degree-modulated laser coagulation is possible for all coagulation sites. The size of the individual spots can be varied to a large extent; preferably the diameters are in a range between 50-1000 p.m. Thereby, the size of the individual spots can be modulated within a series of individual spots (which can be designed particularly as a straight line) or through a change of the sizes of the individual spots from line to line.

In addition to a preferably homogenous laser therapy of the retina with a predetermined equidistant grid, a predetermined equal temperature, and a predetermined equal treatment depth due to the applied wavelength, a multidimensional modulation of the degree of treatment of the retina is also possible with a system, according to the invention, which exhibits a monochromatic laser or a polychromatic laser system, an ophthalmic scan system, and a temperature measuring system. For example, this can result in the same therapeutic benefit for the patient without having to completely coagulate excessively large areas of the retina and to lose said areas for the ability to see. Simultaneously, however, a retinal detachment and therefore aggravated progress of the disease is avoided.

For example, this is possible because classic coagulation spots are set in a rough grid and sub-coagulative treatment occurs in the intermediate spaces without damage to the photoreceptors. Thereby, this method is possible line by line or within a pattern.

A selective retina therapy can also be performed on the basis of a μ-second laser pulses. Thereby, the selective absorption of the particularly green laser light is utilized within the retinal pigment epithelium and ensures by means of the temporally limited exposure in the μ-second range that, within the thermal relaxation time, almost the entire heat remains in the selectively absorbing pigment epithelium and does not reach the photoreceptor layer. This induces the damaged pigment epithelium to regenerate without showing any visible damage in the fundus image.

A different selective retinal therapy is executed in planar fashion by application of a scanned CW laser beam. Thereby, the exposure time is appropriately limited through the scanning speed within the thermal relaxation time.

With a controlled, selective retina coagulation, different absorption properties in the retinal pigment epithelium and different local transmissions of the ocular media are taken into account. As a result, locally different zones of damage of the retinal pigment epithelium can be treated.

An optoacoustic measuring system or an optical measuring system, for example, are used as temperature measuring system. By choosing a wavelength in the yellow, green, red, or infrared spectral range, a homogenous coagulation depth or hyperthermia depth can be set. Choosing equidistant individual spot distances and their diameters allows for a structuring of the homogeneity within the surface.

A targeted planning of the treatment for the best possible individual therapy is possible due to diagnostic data ascertained beforehand. Such data were ascertained particularly on the basis of fundus images (color images, angiography images, autofluorescence images, etc.), OCT images (optical coherence tomography), or confocally scanned images. Subsequently, the treatment is performed by a partly or fully automated generation of treatment parameters and a partly or fully automated execution of the treatment.

The following lasers are used: E.g., argon lasers, diode lasers, diode-pumped solid-state lasers, diode-pumped semiconductor lasers, fiber lasers, and frequency-doubled Nd:YAG lasers. The lasers can be applied as pulsed laser or CW laser.

The programmed control unit is preferably designed as hard-wired programmed or stored-program controller. Preferably, the controller exhibits a processor architecture.

The positioning of the focused laser beam is effected automatically or semiautomatically by use of deflection elements which can deflect the beam two-dimensionally. For example, this can be effected through galvanometric mirror scanners, piezo-driven optical elements, acousto-optical elements, electro-optical elements, or laterally moving lenses. Thereby, the beam positioning elements can move the beam in a translative, torsional, tilted, or rotating fashion. Said elements can be reflecting as well as refractive in transmission.

The therapy beam is either parallel or bundled. For example, it exhibits an elliptic, preferably circular polarization. However, it is also possible to use linearly polarized or unpolarized therapy beams.

BRIEF DESCRIPTION OF THE DRAWINGS

Further details of the invention are described as follows by means of the attached figures.

DETAILED DESCRIPTION

Figure 1:
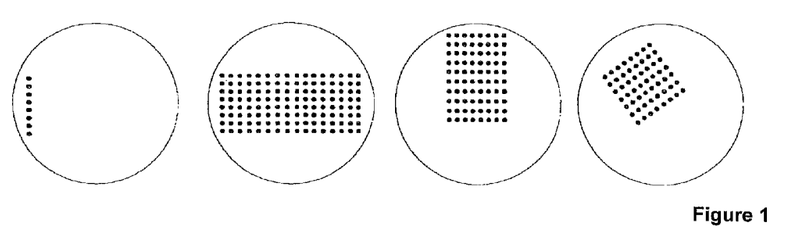
FIG. 1 shows a series of patterns of individual spots originating from one another through translation.

FIG. 1 shows in the first depiction from the left the basic form of a sequential, one-dimensional series of individual spots, which serves as starting point for the additional depictions of FIG. 1 and their multiple applications, as described in the following.

The series consists of eight individual spots which are arranged equidistantly to one another and run in vertical direction. The first individual spot is the depicted individual spot in the top position. Starting with said spot, the sequence is generated continuously from top to bottom in the depicted order.

Starting from said basic form, a pattern of individual spots—depicted in the second drawing from the left—arranged equidistantly to one another in a 7×16 matrix is obtained through a translation of the basic vertical series in the left drawing.

Deviating from the basic form depicted in the first drawing from the left, the sequential, one-dimensional series can also exhibit a horizontal or other direction. Starting with the respective basic form, the patterns depicted in the additional drawings in FIG. 1 can be obtained. Thereby, the size of the matrix of individual spots arranged equidistantly to one another depends on the number of translations.

Figure 2:
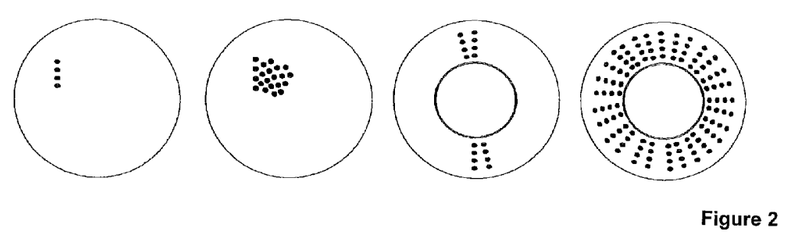
FIG. 2 shows a series of patterns of individual spots originating from one another through rotation.

The left drawing of FIG. 2 shows a shortened initial sequence with four individual spots when compared to the basic sequence in FIG. 1 with eight individual spots. The pattern in the second depiction from the left is obtained from the basic sequence in the left depiction in such a way that advancing from left to right one rotation each is achieved around a rotation center (not depicted) with an alternating sequence length between three and four individual spots, wherein the sequences with three individual spots are set in the gaps of the sequences with four individual spots. This is achieved in such a way that, in addition to the rotation, a translation of the initial individual spots is additionally executed in transverse direction.

By contrast, the second drawing from the right in FIG. 2 shows a plain rotation between the first series of individual spots running in vertical direction and the second series slightly rotated counterclockwise as a result. The initial series—as in FIG. 1—also exhibits eight individual spots, but the distance between the fourth and fifth individual spot is significantly greater. Said distance is chosen in such a way that no individual spots are present in a depicted circle. The rotation center is also the center of the depicted circle. A continuous and repeated rotation around the same angle of rotation indicated in the second drawing from the right in FIG. 2 results in the radial drawing on the right in FIG. 2.

Figure 3:
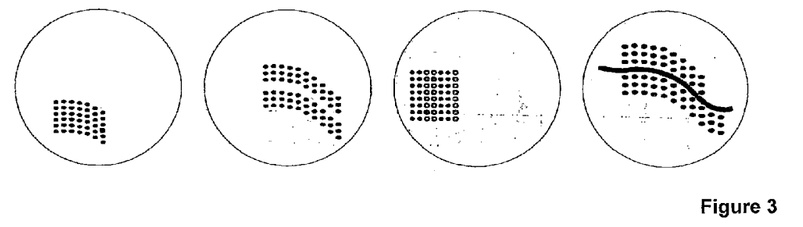
FIG. 3 shows a series of patterns of individual spots originating through translation and change of the initial position as well as omission of a spot sequence.

An irregular translation (which can also be called a modification of the initial position) is executed in the two left drawings in FIG. 3. Thereby, a vertical initial series of five individual spots is shown in the left drawing.

The second drawing from the left shows a vertical initial series of six individual spots which—similar to the two drawings on the right of FIG. 2—exhibits an increased distance between the upper half and the lower half (inner sequence distance) of the respective three individual spots.

However, in the third drawing from the left in FIG. 3, a vertical series of seven individual spots is completed to a pattern through a consistent translation; however, said pattern is altered in respect of the form of the individual spots between the first and second (as well as the fifth and sixth) series relative to the third and fourth (as well as the seventh) series in such a way that the latter spot positions can be omitted by the operator, i.e., they do not constitute coagulation sites.

The right drawing in FIG. 3 shows a special application, wherein the grey line represents a blood vessel. The operator omits those spot positions which would impinge on the blood vessel.

Figure 4:
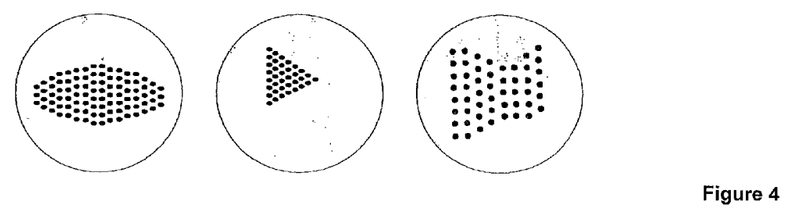
FIG. 4 shows two patterns of individual spots originating through translation and change of the length of the sequence.

In the two drawings on the left in FIG. 4, translations and changes in the sequence length with vertical symmetry of the spot sequence are superimposed. In the right drawing this leads to a pattern which represents a triangle with decreasing sequence length from left to right.

In the drawing on the right in FIG. 4, a translation is also superimposed with a change of the sequence length of the spot sequence but the sequence length varies due to the absence of symmetry.

Figure 5:
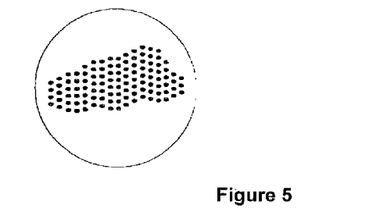
FIG. 5 shows a pattern of individual spots originating through translation, change of the starting point and length of the sequence.

FIG. 5 shows an irregular pattern which is obtained through the initial series of four vertical individual spots, as depicted on the very left, through varying the sequence length, translation, and change of the initial positions.

Figure 6:
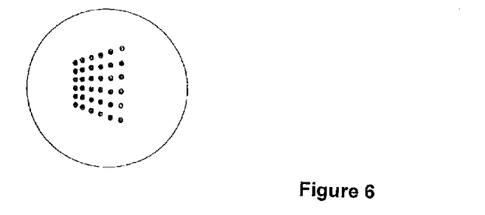
FIG. 6 shows a pattern of individual spots originating through translation and change of the distances between the individual spots.

FIG. 6 shows a pattern which is formed through translation of a basic form in vertical direction. Contrary to the previous patterns, the distances of the individual spots of the basic form are changed with every translation, resulting in a pattern in the form of a "fanned out" 6×6 matrix.

Figure 7:
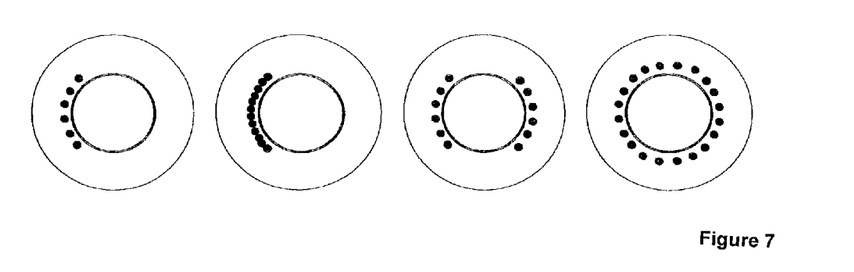
FIG. 7 shows patterns of individual spots originating through rotation of individual spots arranged on a circular arc.
Figure 8:
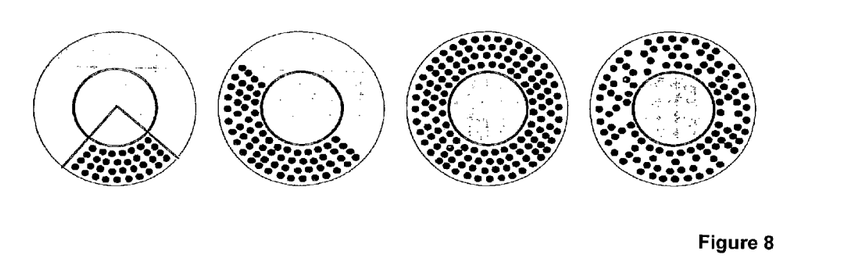
FIG. 8 shows patterns of individual spots originating through rotation of individual spots arranged as circle segment.

The patterns in FIG. 7 and FIG. 8 are, in contrast to the previously described patterns, not based on the basic form of a sequential, one-dimensional series of individual spots in accordance with the drawing on the left in FIG. 1. Similar to the two drawings on the right in FIG. 2, no individual spots are present within the depicted circle.

The drawing on the left in FIG. 7 shows the applied basic form as a circular arc of individual spots. Through a slight rotation, this basic form in the form of a circular arc results in the pattern depicted in the second drawing from the left, and a 180° rotation results in the pattern depicted in the third drawing from the left. Through multiple rotations in conjunction with the omission of spot positions by the operator, said basic form can be completed to a pattern in the form of a full circle.

According to the drawing on the left in FIG. 8, a circular segment, wherein individual spots are arranged, is used as basic form in this embodiment. Starting with said basic form in the form of a circular segment, the pattern depicted in the second drawing from the left can be produced with a single rotation, and the third drawing from the left can be produced through multiple rotations. As can be seen in the drawing on the right in FIG. 8, the patterns can be reduced once again by the operator through omission of spot positions. Preferably, the inner arc forms the basic sequence in the circular segment. In order to "fill" the circular segment, the following sequence is produced on a greater radius, wherein, as a rule, the distance and the number of individual spots in the basic sequence are enlarged. This approach is advantageous because the innermost arc, i.e., the basic sequence, is placed near the macula where the demands are highest. Said demands decrease accordingly in the outward direction.

The patterns shown in FIGS. 1 to 8 are only exemplary and can be modified arbitrarily for producing any desired pattern. This allows for a precise response to the individual case to be treated and for setting the patterns in such a way that coagulation occurs solely at the required coagulation points. The individual spots shown in FIGS. 1 to 8 are produced by the pilot beam, and the therapy beam will subsequently coagulate said sites.

Figure 9:
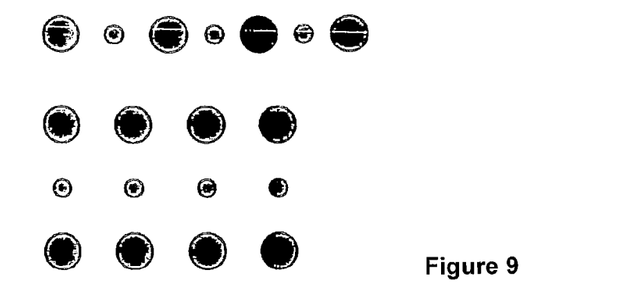
FIG. 9 shows a pattern of coagulation sites originating through lateral change, change of size, change of the length of the sequence and the inner sequence distance.

Based on a series of individual spots in horizontal direction, FIG. 9 shows a pattern, wherein the uppermost row was altered through modification of the sequence length as wells as the inner sequence distances. However, these are not the points marked by the pilot beam but the coagulation sites subsequently caused by the therapy beam. Hereby, the coagulation sites are varied according to the respective size of the coagulation site required for the individual case. Preferably, the diameters of such coagulation sites range from 50 to 500 μm.

In addition to a translation in vertical direction, a change of the diameter of the individual spots was also made between the lowest and second to lowest (and also between the second to lowest and second to highest) series of individual spots. However, between the second series from the top and the uppermost series, not only a partial change of the diameter of the individual spots was made (i.e., every other individual spot was reduced from the size in the second series from the top to a size according to the second series from the bottom) but also a sequence extension from four to seven individual spots as well as a change in the inner sequence distances was executed.

Figure 10:
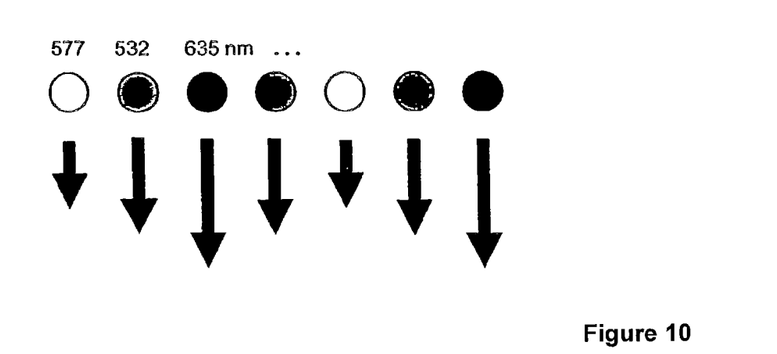
FIG. 10 shows a series of coagulation sites which are coagulated with different wavelengths.

FIG. 10 shows a grid of coagulation points with equal diameters which were irradiated with different wavelengths. Hereby, a wavelength of 577 nm was used for yellow light (550-580 nm), a wavelength of 532 nm for green light (514-550 nm), and a wavelength of 659 nm for red light (630-680 nm). The series from left to right is as follows: Yellow, green, red, green, yellow, green, red. Due to the different applied wavelengths, the primary absorption of energy in the retina takes place in different depths. As a result, coagulation occurs in the upper area of the retina due to the highest absorption of the blood pigment hemoglobin in the yellow spectral range. The highest absorption in the green wavelength range is caused by the photopigment melanin, resulting in coagulation in the medium depth of the retina. Red wavelengths cause the deepest penetration in the retina, resulting in the highest degree of coagulation.

Due to the targeted irradiation of different coagulation sites with different wavelengths (colors), a depth modulation can be achieved. As a result, the individually required treatment can be taken into account.

Figure 11:
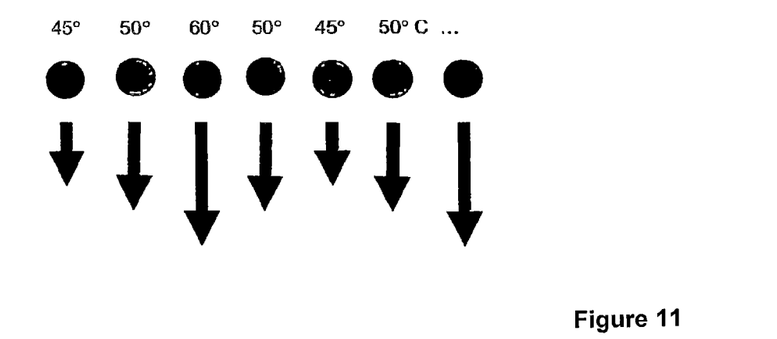
FIG. 11 shows a series of coagulation sites which are coagulated through different temperatures.

FIG. 11 shows the same row of coagulation sites as FIG. 10. However, in FIG. 11, a modulation with different coagulation temperatures instead of different light wavelengths is executed. Hereby, coagulation occurs monochromatic at a wavelength of, e.g., 532 nm (i.e., in the green wavelength range). Due to the different coagulation temperatures of, e.g., 45°, 50°, 60°, different degrees of coagulation are achieved within the depicted coagulation sites. Thereby, the length of the arrows indicates the degree of coagulation in the retina, wherein long arrows represent a higher degree of coagulation than shorter arrows. This results in an equidistant, monochromatic coagulation degree-modulated laser coagulation or hyperthermia.

Figure 12:
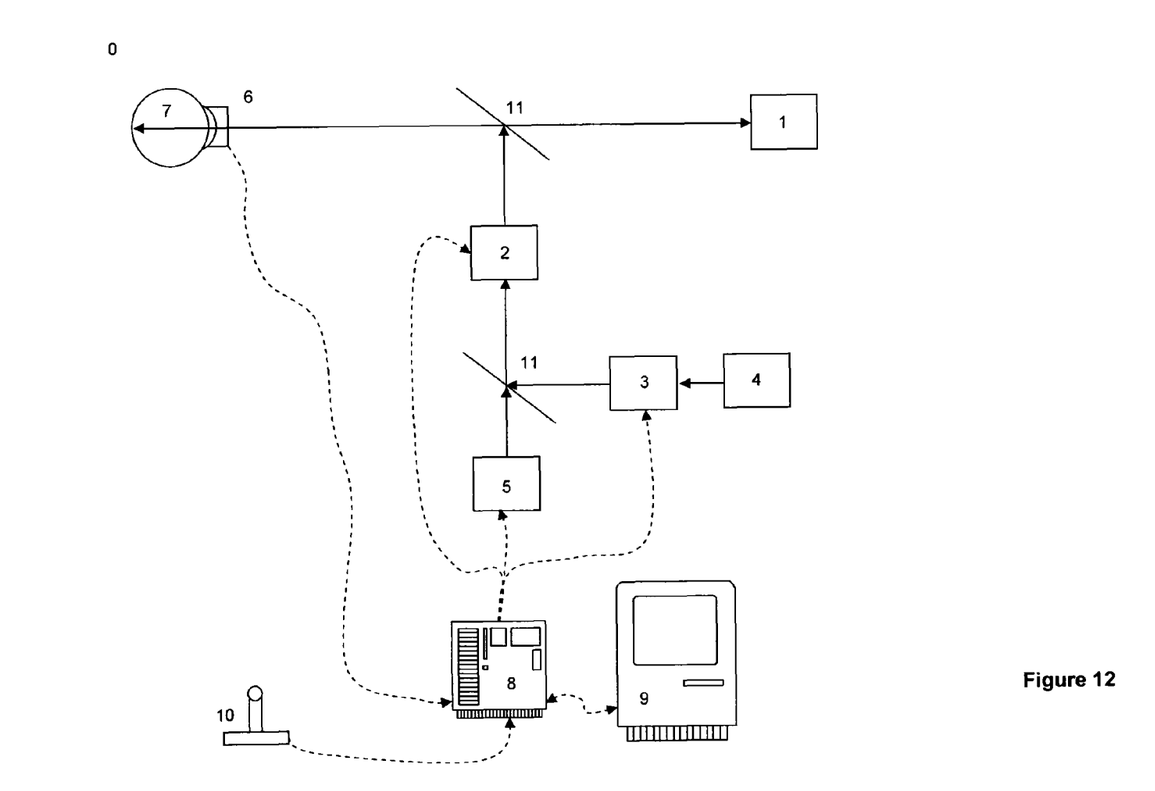
FIG. 12 depicts a system for coagulating the retina according to an example embodiment of the invention.

Referring to FIG. 12, in an example embodiment, the system for coagulating the retina, having an imaging diagnostic unit 1, a therapy beam source 4 emitting a pilot beam for coagulating coagulation sites, a pilot beam source 5 emitting a pilot beam for marking the coagulation sites by means of a spot sequence, a beam deflecting unit 2 for generating the spot sequence and for positioning the therapy beam, an electronic control unit 8 for controlling the above devices, a software interface 9, and an interactive interface 10, is used for executing the method described above.

By application of the imaging diagnostic unit, the operator can determine prior to executing the coagulation, at which concrete site of the retina said coagulation should be performed since the spot sequences marked by the pilot beam can now be observed. The therapy beam is used for coagulating the coagulation sites which were marked with the pilot beam beforehand. Therapy beam and pilot beam are controlled by beam deflecting unit 2 in such a way that the spot sequences of the pilot beam are projected onto the retina and that the therapy beam performs the coagulation on the marked individual spots after clearance through the confirmation by reception of the confirmation signal. The entire process is controlled by the control unit 8 which particularly controls the activation of the therapy beam source 4 as well as the beam deflection within the beam deflecting unit 2. The entire process is executed via a software interface 9. By use of the interactive interface 10, the confirmation by means of the confirmation signal is effected which is necessary for activating the therapy beam source 4 once the marking of the individual spots of the coagulation sites were indicated to the operator by use of the pilot beam.

For example, the imaging diagnostic unit 1 is a laser slit lamp, a fundus camera, or a scanning laser ophthalmoscope.

A number of therapy beam sources 4 light sources, such as LEDs, superluminescent diodes, gas discharge lamps, and particularly lasers are suited to emit the therapy beam. Thereby, a multiwavelength laser, which can emit different colors in the visible range, is used, for example. Particularly examples are the colors green, yellow, and red. Furthermore, it is also possible for the multiwavelength laser to emit light in the near infrared range. The different indicated wavelengths make it possible to reach different coagulation depths. Due to the photopigment melanin, the highest absorption takes place in the green wavelength range (from 514-550 nm); the highest absorption of the blood pigment hemoglobin is achieved in the yellow spectral range (550-580 nm); however, coagulation at a high tissue penetration takes place because of the red wavelengths (630-690 nm) or by means of a wavelength in the near infrared range (e.g., at 810 nm).

For coagulating the retina, pulse durations between 10 ms and 100 ms, particularly between 20 ms and 50 ms, have proven successful for the therapy beam.

Even though pulse durations below 20 ms ensure an almost painless treatment, the effect of the treatment must be expected to be inferior. By contrast, a superior treatment effect must be expected with pulse durations above 50 ms but which can lead to scarring of the treated sites.

A high coagulation effect, wherein resulting scarring diminishes over time, is achieved with pulse durations between 20 ms and 50 ms. Therefore, pulse durations between 20 ms and 50 ms are recommended for the solution of coagulating the retina as described herein.

A further embodiment of the invention provides for the pilot beam to be a laser diode which for example radiates in the red range. The resulting markings on the retina—as already described above—are easily identifiable by the operator.

A further embodiment of the invention provides for the beam deflecting unit 2 to coaxially project the pilot beam and the therapy beam onto the retina. This ensures that the coagulation by means of the therapy beam takes place exactly at the position indicated beforehand by the pilot beam to the operator who cleared said position by entering of a confirmation signal. This ensures that the retina is not coagulated in sites which should not be coagulated, for example, because they still contain unimpaired tissue.

A further embodiment of the invention provides for the beam deflecting unit 2 to exhibit movable lenses, mirrors, or diffractive beam splitters in the beam path. In prior art, these are well-known, reliable devices for beam deflection. Said lenses or mirrors are preferably controlled via motors; this particularly refers to galvanometrically controlled mirrors, piezo scanners, or micromirror arrays.

A further advantageous development of the invention provides for the control unit 8 to be a microcontroller which exhibits at least one input interface and one output interface and which is programmable. This allows for previously determined values about the retina to be treated as well as the present ocular media to be entered into the control unit, which therefore knows the individually required data for the pending treatment and can adjust the respective series of individual spots to the present concrete conditions. As a result, it will not be necessary for the operator to periodically refuse clearance of the displayed series of individual spots and for the system to calculate and display to the operator an alternative series. Instead, every one of the displayed series can be cleared by the operator, leading to an accelerated treatment as well as increased reliability of the treatment.

A further advantageous development of the invention provides also for an interrupter 3 which prevents at least one specific wavelength range of the therapy beam from impinging on the coagulation site. As already described above, the penetration of the radiation of the therapy beam, and therefore the coagulation, can be controlled through the use of different wavelengths. Therefore, the interrupter 3 specifies different penetration depths of the therapy beam at a predetermined individual spot or for an entire series of individual spots. In one example, said interrupter 3 is a filter which can be introduced into the therapy beam.

A further advantageous development of the invention provides for the interrupter 3 to be a device which deactivates the therapy beam, particularly in the form of an aperture in the area through which the therapy beam passes. As a result, the coagulation can be altogether completed and not only selectively in one or different depths as is the case with the previously described filter.

A further advantageous development of the invention additionally provides for a device for temperature determination 6 for determining the temperature at the coagulation site while the therapy beam is directed at said site. As already described above, the photoreceptor layer above the pigment epithelium to be treated can thereby be excluded from damage. Temperature determination is preferably effected by means of a detector 6 within the device for temperature determination, which records pressure waves from the coagulation site. Since the device for temperature determination is connected to the interrupter 3, the therapy beam can immediately be deactivated once the predetermined temperature is reached, resulting in the above-mentioned effect, i.e., the photoreceptor layer will not be damaged. Hereby, an indirect connection of the device for temperature determination 6 via the control unit can be provided in addition to the direct connection to the interrupter 3.

A further advantageous development of the invention provides for the system to be prepared for irradiating every individual spot of the serial spot sequence through the therapy beam with an individual size, form, wavelength, and duration. This also serves the individual treatment of every site of the retina. By means of size and form, the treatment area at the respective site can be precisely adjusted to the desired size and form. By the wavelength adjustment, a specific depth of coagulation can be achieved within the retina, as already described above. As a result, a depth-modulated laser coagulation is possible for all coagulation sites. Through adjusting the duration, the temperature of the individual coagulation sites can be varied, resulting in the degree of coagulation of the retina. Therefore, a coagulation degree-modulated laser coagulation is possible for all coagulation sites. The size of the individual spots can be varied to a large extent; preferably the diameters are in a range between 50-1000 μm. Thereby, the size of the individual spots can be modulated within a series of individual spots (which can be designed particularly as a straight line) or through a change of the sizes of the individual spots from line to line.

The invention claimed is:

1. A method for marking coagulation sites on a retina by application of a light source, comprising:
    projecting a serial spot sequence of the light source formed of a sequential, one-dimensional series of individual spots on the retina by use of a beam deflection unit, wherein the individual spots indicate the coagulation sites during a marking and treatment sequence;
    waiting for confirmation of the sequence of individual spots by entry of a confirmation signal from an operator during the marking and treatment sequence;
    after receiving the confirmation of the sequence of the individual spots, recalculating an automated sequence of steps having a further serial spot sequence and further projection of the further serial spot sequence on the retina according to the projecting a serial spot sequence;
    and, subsequently, repeating of the waiting for confirmation of the further sequence of individual spots by entry of a confirmation signal and the after receiving the confirmation of the sequence of the individual spots, recalculating the automated sequence of steps having a further serial spot sequence and projection of the serial spot sequence on the retina according to the projecting a serial spot sequence.

2. The method according to claim 1, further comprising locating the sequential, one-dimensional series of individual spots at equidistant distances, a progression of which can be straight or curved as well as continuous or non-continuous and which can be applied randomly.

3. The method according to claim 1, further comprising applying a temporal series of the spot sequence such that an interval between the individual spots is between 1 ns and 5 s.

4. The method, according to claim 3, further comprising applying the temporal series of the spot sequence such that the interval between the individual spots is between 1 μs and 1 s.

5. The method according to claim 3, further comprising applying a temporal series of the spot sequence such that the interval between the individual spot is between 40 ms and 0.5 s.

6. The method according to claim 1, further comprising performing an automated sequence of steps that provides for an equidistant translation and/or rotation.

7. The method according to claim 1, further comprising selecting the light source such that the light source radiates laser light.

8. The method according to claim 7, further comprising selecting the light source such that the light source radiates laser light in the red range.

9. The method according to claim 1, further comprising varying one or several laser parameters prior to the confirmation of the next spot sequence by active influence of an operator.

10. The method according to claim 1, further comprising receiving the confirmation signal from a joystick, voice recognition, or a foot switch.

11. The method according to claim 10, further comprising receiving the confirmation signal from a multimodal foot switch.

12. The method according to claim 1, further comprising receiving the confirmation only after a change of position of the recalculated spot sequence.

13. The method according to claim 1, further comprising arranging a distance of a next spot sequence from a previous spot sequence to be between zero and ten times that of a spot diameter.

14. The method according to claim 13, further comprising arranging the distance of a next spot sequence from a previous spot sequence to be between 0.8 and 1.5 times the spot diameter.

15. The method according to claim 1, further comprising initiating a change of a distance of starting position, orientation, length, inner-sequence distance, type of spot sequence, rotation, translation and/or step length of the spot sequence with reference to a previous spot sequence by receiving input from an operator and/or based on previously determined examination data of the retina.

16. The method according to claim 1, further comprising initating temperature determination of the individual spot during the use of a therapy beam.

17. The method according to claim 16, further comprising deactivating the therapy beam when a predetermined temperature is reached.

18. The method according to claim 16, further comprising making the predetermined temperature identical for all individual spots.

19. The method according to claim 16, further comprising making the individual spots encircle the coagulation sites.

* * * * *

UNITED STATES PATENT AND TRADEMARK OFFICE
CERTIFICATE OF CORRECTION

PATENT NO.         : 8,986,289 B2                         Page 1 of 1
APPLICATION NO.    : 13/320727
DATED              : March 24, 2015
INVENTOR(S)        : Gerald Kunath-Fandrei et al.

It is certified that error appears in the above-identified patent and that said Letters Patent is hereby corrected as shown below:

Specification

Col. 1, line 45, delete second occurrence of "is" and insert --in--

Col. 6, line 52, delete "p.m." and insert --µm--

Col. 10, line 32, delete "wells" and insert --well--

Signed and Sealed this
First Day of March, 2016

Michelle K. Lee
*Director of the United States Patent and Trademark Office*